United States Patent
Ishikawa

(10) Patent No.: US 10,299,710 B2
(45) Date of Patent: May 28, 2019

(54) ORGANISM OPTICAL MEASUREMENT DEVICE

(75) Inventor: Akihiro Ishikawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 1074 days.

(21) Appl. No.: 13/384,813

(22) PCT Filed: Jul. 21, 2009

(86) PCT No.: PCT/JP2009/063026
§ 371 (c)(1),
(2), (4) Date: Jan. 19, 2012

(87) PCT Pub. No.: WO2011/010355
PCT Pub. Date: Jan. 27, 2011

(65) Prior Publication Data
US 2012/0191359 A1    Jul. 26, 2012

(51) Int. Cl.
*A61B 5/1455*    (2006.01)
(52) U.S. Cl.
CPC .. *A61B 5/14553* (2013.01); *A61B 2562/0233* (2013.01); *A61B 2562/046* (2013.01)
(58) Field of Classification Search
CPC . A61B 5/0059; A61B 5/14553; A61B 5/0476; A61B 5/6822
USPC .................................................. 600/310–344
See application file for complete search history.

(56) References Cited

U.S. PATENT DOCUMENTS

| 2006/0100526 A1* | 5/2006 | Yamamoto ............. A61B 5/064 600/476 |
| 2007/0083097 A1 | 4/2007 | Fujiwara et al. |

FOREIGN PATENT DOCUMENTS

| JP | 2006-109964 A | 4/2006 |
| JP | 2006-187306 A | 7/2006 |
| JP | 2006-218196 A | 8/2006 |
| JP | 2008-86407 A | 4/2008 |
| JP | 2009-95380 A | 5/2009 |

* cited by examiner

*Primary Examiner* — Eric F Winakur
*Assistant Examiner* — Marjan Fardanesh
(74) *Attorney, Agent, or Firm* — McDermott Will & Emery LLP

(57) ABSTRACT

An organism optical measurement device having a light transmitter/receiver control unit for obtaining measurement data concerning brain activities and a measurement data display control unit for displaying the measurement data. The organism optical measurement device is further provided with a head surface appearance image acquiring unit for acquiring a head surface appearance image of a subject, a head surface appearance image display control unit for displaying the head surface appearance image, and a measurement-related position calculating unit for calculating the measurement-related position in the head surface appearance image from which the measurement data is obtained when an input device specifies the positions in the head surface appearance image corresponding to the positions of a light transmitting probe and a light receiving probe disposed on the head surface of the subject. The measurement data display control unit displays the measurement data in the measurement-related position in the head surface appearance image.

4 Claims, 8 Drawing Sheets

ORGANISM OPTICAL MEASUREMENT DEVICE

CROSS REFERENCE TO PRIOR APPLICATIONS

This application is a U.S. National Phase application under 35 U.S.C. § 371 of International Application No. PCT/JP2009/063026, filed on Jul. 21, 2009. The International Application was published in Japanese on Jan. 27, 2011 as WO 2011/010355 A1 under PCT Article 21(2). All of these applications are herein incorporated by reference.

TECHNICAL FIELD

The present invention relates to an organism optical measurement device for non-invasively measuring brain activities, and in particular, an organism optical measurement device which measures a chronological change in the blood flow in each section within a brain and a chronological change the oxygen supply, and this can be used as an oxygen monitor for diagnosing whether or not the tissue of a living body is normal.

BACKGROUND

Hemoglobin plays a role to carry oxygen in blood. The concentration of hemoglobin in blood fluctuates in accordance with the duration and contraction of vessels, and therefore it is known that the duration and contraction of vessels can be detected by measuring the concentration of hemoglobin.

Thus, an organism measuring method is known for simply and non-invasively measuring the inside of an organism using light by employing the fact that the concentration of hemoglobin corresponds to the oxygen metabolizing function inside an organism. The concentration of hemoglobin can be found from the amount of light that is gained when transmitted through an organism when the organism is irradiated with light of which the wavelength ranges from that of visible light to near infrared rays.

Furthermore, hemoglobin combines with oxygen so as to be oxyhemoglobin (hereinafter referred to as oxyHb), and conversely detaches from oxygen so as to be deoxyhemoglobin (hereinafter referred to as deoxyHb). It is also known that within a brain, oxygen is supplied to a portion that is activated through a blood flow redistributing effect, and the concentration of oxyhemoglobin that has combined with oxygen increases. Therefore, the measurement of the concentration of oxyhemoglobin can be applied to the observation of brain activities. Oxyhemoglobin and deoxyhemoglobin have different absorption spectra for light ranging from visible light to near infrared rays, and therefore, the concentration of oxyhemoglobin and the concentration of deoxyhemoglobin can be found by using two types of near infrared rays having different wavelengths, for example.

Thus, an organism optical measurement device having a light transmitting probe and a light receiving probe has been developed in order to non-invasively measure brain activities. In the organism optical measurement device, the light transmitting probe disposed on the surface of the head of a subject irradiates the brain with near infrared rays, and at the same time, the light receiving probe disposed on the surface of the head detects the amount of near infrared rays emitted from the brain. Near infrared rays transmit through the scalp tissue and the bone tissue and are absorbed by the oxyhemoglobin and deoxyhemoglobin in blood. Therefore, the light transmitting probe and the light receiving probe can be used to find chronological changes in the concentration of oxyhemoglobin, the concentration of deoxyhemoglobin, and the total concentration of hemoglobin that can be calculated from these in the measured portion in the brain as the measurement data. FIG. 6 is a graph showing an example of the measurement data. Here, the longitudinal axis shows the concentration and the lateral axis shows the time.

Here, the relationship between the measured portion in the brain and the distance (channel) between the light transmitting probe and the light receiving probe is described. FIG. 7($a$) is a cross-sectional diagram showing the relationship between the measured portion in the brain and the pair of probes, light transmitting probe and light receiving probe, and FIG. 7($b$) is a plan diagram of FIG. 7($a$).

The light transmitting probe 12 is pressed against the light transmitting point T on the surface of the head of a subject, and at the same time, the light receiving probe 13 is pressed against the light receiving point R on the surface of the head of the subject. Thus, light is irradiated from the light transmitting probe 12, and at the same time, the light receiving probe 13 detects the light emitted from the surface of the head. At this time, the light that has passed through the banana-shaped region (measurement region) after being irradiated through the light transmitting point T on the surface of the head reaches the light receiving point R on the surface of the head. As a result, information gained from the amount of light received particularly by the portion S of the subject (concentration of oxyhemoglobin, concentration of deoxy hemoglobin, and total concentration of hemoglobin calculated from these) can be found in the measurement region where the portion S is located at a depth L/2, which is half of the shortest length of the line connecting the light transmitting point T and the light receiving point R along the surface of the head of the subject from the middle point M of the shortest length L of the line connecting the light transmitting point T and the light receiving point R along the surface of the head of the subject.

In recent years, organism optical measurement devices that can be applied in the medical field, such as brain function diagnosis and circulatory disorder diagnosis, measuring the concentration of hemoglobin in the measured portion in the brain relating to the brain functions, such as motion, sense and thought, have been developed. Such organism optical measurement devices have been applied to near infrared spectrometric analyzers, for example (see Japanese Unexamined Patent Publication 2006-109964).

In near infrared spectrometric analyzers, a holder is used so that a number of light transmitting probes and a number of light receiving probes can be made to make close contact with the surface of the head of a subject in a predetermined arrangement. An example of this holder is a mold holder that has been molded in bowl form so as to fit on the surface of a head. A number of through holes are provided in the mold holder, and the light transmitting probes and the light receiving probes are inserted into these through holes so that the channels become constant and information can be gained from the amount of light received at a specific depth from the surface of the head.

FIG. 8 is a plan diagram showing the positional relationships of 12 light transmitting probes and 12 light receiving probes in a near infrared spectrometric analyzer as described above. Light transmitting probes 12$a$ to 12$l$ and light receiving probes 13$a$ to 13$l$ are aligned so as to alternate in the diagonal directions. Here, light irradiated from the light transmitting probes 12$a$ to 12$l$ can be detected by the light receiving probes 13$a$ to 13$l$, which are not adjacent to the light transmitting probes 12a to 12l, but here, only the adjacent light receiving probes 13a to 13l can detect the light in order to make the description simple. Thus, 36 pieces of information (measurement data) can be gained from the amount of light received.

Here, the channels are generally 30 mm, and in the case where the channels are 30 mm, information should be able to be gained from the amount of received light at a depth of 15 mm to 20 mm from the middle point of the channels as described above. That is to say, the points at a depth of 15 mm to 20 mm from the surface of the head mostly correspond to the portions on the surface of the brain, and thus, information (measurement data) on the brain activities can be gained from the amount of received light. Thus, the measurement data on the brain activities gained in a near infrared spectrometric analyzer is displayed as an image so that doctors and the like can observe. FIG. 9 is a diagram showing an example of a monitor screen where a conventional organism optical measurement device displays 36 pieces of measurement data.

The monitor screen displays 36 pieces of measurement data #1 to #36. At this time, each piece of measurement data gained when a light receiving probe 13 detects light irradiated from a light transmitting probe 12 is aligned for the display at the middle point of the shortest line connecting the light transmitting probe 12 and the light receiving probe 13 in the plan diagram in FIG. 8. For example, the piece of measurement data #1 when the light receiving probe 13a detects the light irradiated from the light transmitting probe 12a is aligned in the upper left, the piece of measurement data #2 when the light receiving probe 13d detects the light irradiated from the light transmitting probe 12a is aligned beneath the piece of measurement data #1, and the piece of measurement data #7 when the light receiving probe 13a detects the light irradiated from the light transmitting probe 12b is aligned to the right of the piece of measurement data #1, and thus the 36 pieces of measurement data #1 to #36 are aligned.

Though mold holders are used to make 12 light transmitting probes 12 and 12 light receiving probes 13 make close contact with the surface of the head as described above, some light transmitting probes 12 or light receiving probes 13 may not make close contact with the surface of the bead due to hair on the surface of the head. As a result, in some cases, some of the 36 pieces of measurement data #1 to #36 are inaccurate pieces of measurement data. At this time, it cannot easily be determined whether or not a piece of measurement data is inaccurate even in the case where there seems to be an inaccurate piece of measurement data or it is perceived that a certain piece of measurement data is inaccurate.

It is also difficult to find from which measured portion in the brain a certain piece of measurement data is gained because 36 pieces of measurement data #1 to #36 are simply aligned as shown in FIG. 9.

SUMMARY

In order to solve the above-described problem, the present inventors examined the method for displaying measurement data. Then, the inventors found a method for displaying measurement data in the head surface appearance image of a subject as a result of measurement. Thus, doctors and the like can determine which light transmitting probe 12 or light receiving probe 13 is placed in a portion with hair or whether or not a certain light transmitting probe 12 or light receiving probe 13 is placed within a portion with hair when they observe the measurement results, and as a result, which piece of measurement data tends to be inaccurate or the probability of this can be understood. The measured portion in the brain from which a certain piece of measurement data is gained can also be easily understood.

That is to say, the organism optical measurement device according to the present invention is provided with: a light transmitting/receiving unit having a number of light transmitting probes deposited on a surface of the head of a subject and a number of light receiving probes deposited on a surface of the head; a light transmitter/receiver control unit for obtaining measurement data on brain activities by controlling the above-described light transmitting probes and the above-described light receiving probes so that the above-described light transmitting probes irradiate the surface of the head with light and the above-described light receiving probes detect light emitted from the surface of the head; and a measurement data display control unit for displaying the above-described measurement data, and is further provided with: a camera for photographing the surface of the head of the above-described subject; a head surface appearance image acquiring unit for acquiring a head surface appearance image of the above-described subject; a head surface appearance image display unit for displaying the above-described head surface appearance image; and a measurement-related position calculating unit for calculating the measurement-related positions in the head surface appearance image from which the above-described measurement data is obtained when an input device specifies the positions in the head surface appearance image corresponding to the positions of the light transmitting probes and the light receiving probes deposited on the surface of the head of the above-described subject, wherein the above-described measurement data display control unit displays measurement data in the measurement-related positions in the above-described head surface appearance image.

In the organism optical measurement device according to the present invention, the head surface appearance image acquiring unit acquires a head surface appearance image of a subject before a doctor or the like checks the subject. As a result, the head surface appearance image display control unit displays a head surface appearance image.

Thus, the doctor or the like places the light transmitting/receiving unit on the surface of the head of a subject and specifies the positions in the head surface appearance image corresponding to the positions of the light transmitting probes and the light receiving probes deposited on the surface of the head of the subject using the input device. As a result, the measurement-related position calculating unit calculates the measurement related positions in the head surface appearance image from which measurement data is gained.

After that, the measurement data display control unit displays the measurement data in the measurement related positions in the head surface appearance image when the doctor or the like checks the subject. That is to say, the measurement data is overlapped on the head surface appearance image when displayed in the measurement-related positions.

As described above, in the organism optical measurement device according to the present example, measurement data is overlapped on the head surface appearance image when displayed in the measurement-related positions, and therefore, a doctor or the like can easily understand the measured portion in the brain from which the measurement data is obtained and whether or not the measurement data is precise when checking the results of the measurement.

In addition, the organism optical measurement device according to the present invention may further be provided with a camera for photographing the surface of the head.

In addition, in the organism optical measurement device according to the present example, the above-described measurement-related positions are middle points of the shortest lines connecting a position specified by a light transmitting probe and a position specified by a light receiving probe in the above-described head surface appearance image.

Furthermore, in the organism optical measurement device according to the present example, the above-described measurement data is data showing a chronological change in the concentration of hemoglobin.

DETAILED DESCRIPTION

In the following, the examples are described in reference to the drawings. Here, the examples are not limited to the below-described embodiments, and of course includes various modifications as long as the gist of the present invention is not deviated from.

Figure 1:
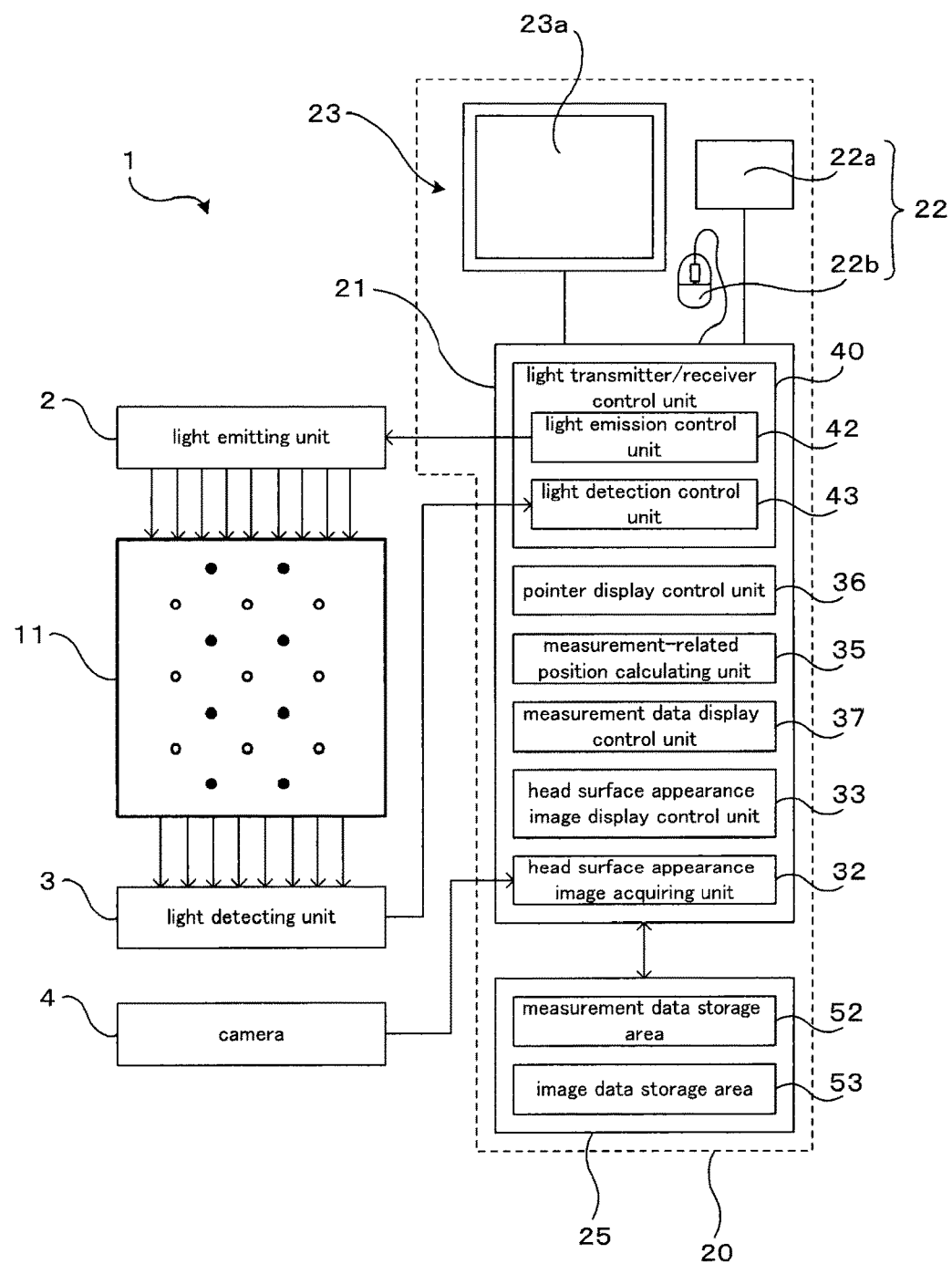
FIG. 1 is a block diagram showing a schematic structure of the organism optical measurement device according to one example.

FIG. 1 is a block diagram showing a schematic structure of the organism optical measurement device according to an example. An organism optical measurement device 1 is formed of a light transmitting/receiving unit 11, a light emitting unit 2, a light detecting unit 3, a camera 4 for photographing the surface of the head of a subject, and a control unit (computer) 20 for controlling the entirety of the organism optical measurement device 1.

Figure 2:
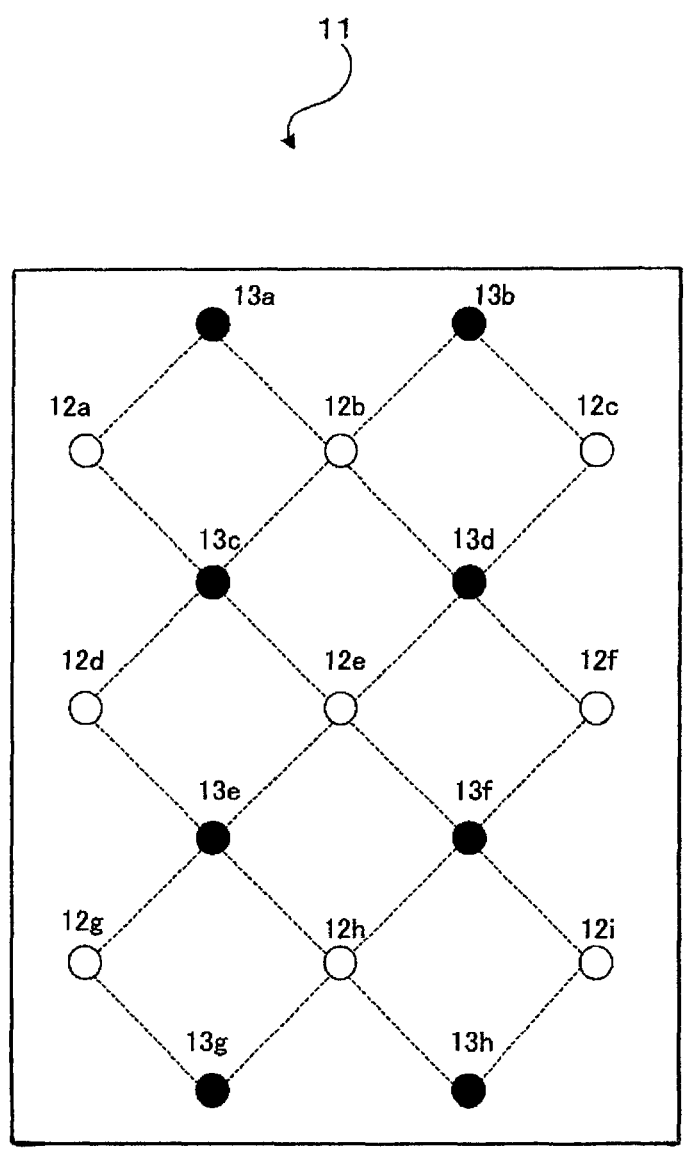
FIG. 2 is a plan diagram showing the positional relationships between nine light transmitting probes and eight light receiving probes in the light transmitting/receiving unit.

In addition, FIG. 2 is a plan diagram showing the positional relationship between nine light transmitting probes 12a to 12i and 8 light receiving probes 13a to 13h in the light transmitting/receiving unit 11.

Figure 3:
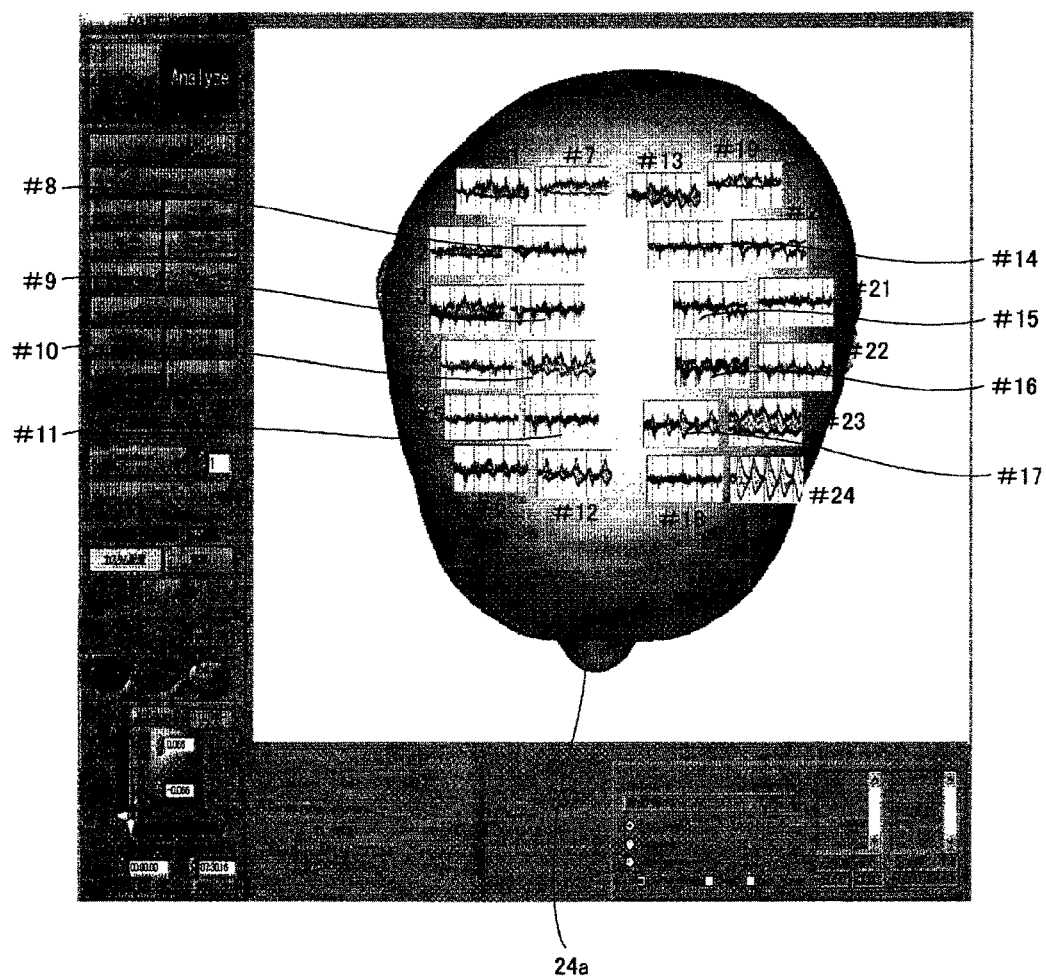
FIG. 3 is a diagram showing an example of a monitor screen for the display in the organism optical measurement device according to the present example.

Furthermore, FIG. 3 is a diagram showing an example of a monitor screen 23a for the display in the organism optical measurement device 1 according to the example. The monitor screen 23a displays a head surface appearance image 24a and 24 pieces of measurement data #1 to #24. Here, FIG. 3 shows the head surface appearance image 24a of a mannequin, and thus, no hair is photographed, but hair may be photographed in actual head surface appearance images 24a.

As shown in FIG. 2, the light transmitting/receiving unit 11 has nine light transmitting probes 12a to 12i and eight light receiving probes 13a to 13h where the light transmitting probes 12a to 12i and the light receiving probes 13a to 13h are arranged so as to alternate in diagonal directions. Here, the distance between the light transmitting probes 12a to 12i and the light receiving probes 13a to 13h is 30 mm. In addition, the nine light transmitting probes 12a to 12i emit light while the eight light receiving probes 13a to 13h detect the amount of light.

The light emitting unit 2 transmits light to one light transmitting probe that is selected from among nine light transmitting probes 12a to 12i by the drive signal inputted through the computer 20. The light used above is near infrared rays (for example, light having two wavelengths, 780 nm and 850 nm).

The light detecting unit 3 detects near infrared rays (for example, light having two wavelengths, 780 nm and 850 nm) received by the eight individual light receiving probes 13a to 13h, and thus outputs eight light receiving signals (measurement data) to the computer 20.

The computer 20 is provided with a CPU 21, and in addition, a memory 25, a display device 23 having a monitor screen 23a or the like, and a keyboard 22a and a mouse 22b, which are input devices 22, are connected to the computer 20.

In addition, the CPU 21 has a light transmitter/receiver control unit 40 for controlling the light emitting unit 2 and the light detecting unit 3, a head surface appearance image acquiring unit 32 for acquiring the head surface appearance image 24a through the camera 4, a head surface appearance image display control unit 33 for displaying the head surface appearance image 24a, a pointer display control unit 36 for displaying a pointer (not shown), a measurement-related position calculating unit 35 for calculating the measurement-related positions, and a measurement data display control unit 37 for displaying the measurement data when the functions resulting from the process of the CPU 21 are illustrated in blocks. Furthermore, the memory 25 has a measurement data storage area 52 for storing the measurement data and an image data storage area 53 for storing the head surface appearance image and the like.

The light transmitter/receiver control unit 40 has a light emission control unit 42 for outputting a drive signal to the light emitting unit 2 and a light detection control unit 43 for storing the measurement data in the measurement data storage area 52 upon reception of a light receiving signal (measurement data) from the light detecting unit 3.

The light emission control unit 42 performs such a control that a drive signal for transmitting light to the light transmitting probe 12 is outputted to the light emitting unit 2.

Upon reception of a light receiving signal from the light detecting unit 3, the light detection control unit 43 performs such a control that eight pieces of measurement data detected by the eight light receiving probes 13a to 13h are stored in the measurement data storage area 52. That is to say, whenever one light transmitting probe transmits light, eight pieces of measurement data are stored in the measurement data storage area 52.

The head surface appearance image acquiring unit 32 performs such a control that a head surface appearance image is acquired from the camera 4 and stored in the image data storage area 53.

The head surface appearance image display control unit 33 performs such a control that the head surface appearance image 24a stored in the image data storage area 53 is displayed on the monitor screen 23a. At this time, the head surface appearance image 24a previously stored in the image data storage area 53 may be used without photographing an image by means of the camera 4 in the case where the subject had been checked in the past.

The pointer display control unit 36 displays a pointer (not shown) on the monitor screen 23a, and at the same time performs such a control that the pointer displayed on the monitor screen 23a is moved or a point is designated by the pointer on the basis of the operation signal outputted from the mouse 22b.

The measurement-related position calculating unit 35 performs such a control that the measurement-related position in the head surface appearance image 24a is calculated when a predetermined position in the head surface appearance image 24a displayed on the monitor screen 23a is designated by the pointer. Typically, a doctor or the like has a subject put the light transmitting/receiving unit 11 on the surface of the head, and after that, designates the positions of the nine light transmitting probes 12a to 12i and the eight light receiving probes 13a to 13h in the head surface appearance image 24a by means of the pointer, while visually comparing the surface of the head on which the light transmitting/receiving unit 11 is placed and the head surface appearance image 24a displayed on the monitor screen 23a and checking the positions of the nine light transmitting probes 12a to 12i and the eight light receiving probes 13a to 13h in the light transmitting/receiving unit 11 placed on the surface of the head of the subject.

At this time, different numbers (T1 to T8) are given to the light transmitting probes $12_{T1}$ to $12_{T8}$ respectively, and at the same time, different numbers (R1 to R8) are given to the light receiving probes $13_{R1}$ to $13_{R8}$ respectively by means of the measurement-related position calculating unit 35 so that the location can be recognized for which light transmitting probe $12_{T1}$ to $12_{T8}$ or light receiving probe $13_{R1}$ to $13_{R8}$ is designated by the pointer, and thus, a doctor or the like designates the location by inputting the corresponding number by means of the keyboard 22a or designates the locations of the light transmitting probes $12_{T1}$ to $12_{T8}$ in the order of the numbers, and then designates the locations of the light receiving probes $13_{R1}$ to $13_{R8}$ in the order of the numbers.

In addition, the doctor or the like prepares a table or the like showing the combinations in advance, which is stored in the memory 25 in the same manner as in the prior art, so that it can be recognized which measurement-related positions between the light transmitting probe $12_{T1}$ to $12_{T8}$ and the light receiving probe $13_{R1}$ to $13_{R8}$ should be calculated by the measurement-related position calculating unit 35.

As a result, on the basis of the table or the like stored in the memory 25 and the designated positions, the measurement-related position calculating unit 35 sets the positions of the middle points of the shortest lines connecting a designated position of a light transmitting probe 12 and a designated position of a light receiving probe 13 as the measurement-related positions in the head surface appearance image 24a in the combinations between the light transmitting probes 12 and the light receiving probes 13 in such a manner that the position of the middle point of the shortest line connecting the designated position of the light transmitting probe 12a and the designated position of the light receiving probe 13a is the measurement-related position in the head surface appearance image 24a in terms of the light transmitting probe 12a and the light receiving probe 13a, the position of the middle point of the shortest line connecting the designated position of the light transmitting probe 12b and the designated position of the light receiving probe 13d is the measurement-related position in the head surface appearance image 24a in terms of the light transmitting probe 12a and the light receiving probe 13d, and the position of the middle point of the shortest line connecting the designated position of the light transmitting probe 12b and the designated position of the light receiving probe 13a is the measurement-related position in the head surface appearance image 24a in terms of the light transmitting probe 12b and the light receiving probe 13a.

The measurement data display control unit 37 acquires information (measurement data) on the amount of light transmitted from a light transmitting probe 12 and received by the light receiving probe 13 that is adjacent to the light transmitting probe 12 from the measurement data stored in the measurement data storage area 52 and finds the concentration of oxyhemoglobin, the concentration of deoxyhemoglobin and the total concentration from the intensity of the transmitted light having the respective wavelength (wavelength of light absorbed by oxyhemoglobin and wavelength of light absorbed by deoxyhemoglobin) on the basis of the acquired measurement data, and at the same time, performs such a control that the measurement data is displayed in the measurement-related positions on the basis of the measurement-related positions calculated by the measurement-related position calculating unit 35. As shown in FIG. 3, for example, pieces of measurement data #1 to #24 are displayed in the measurement-related positions on the head surface appearance image 24a.

Figure 4:
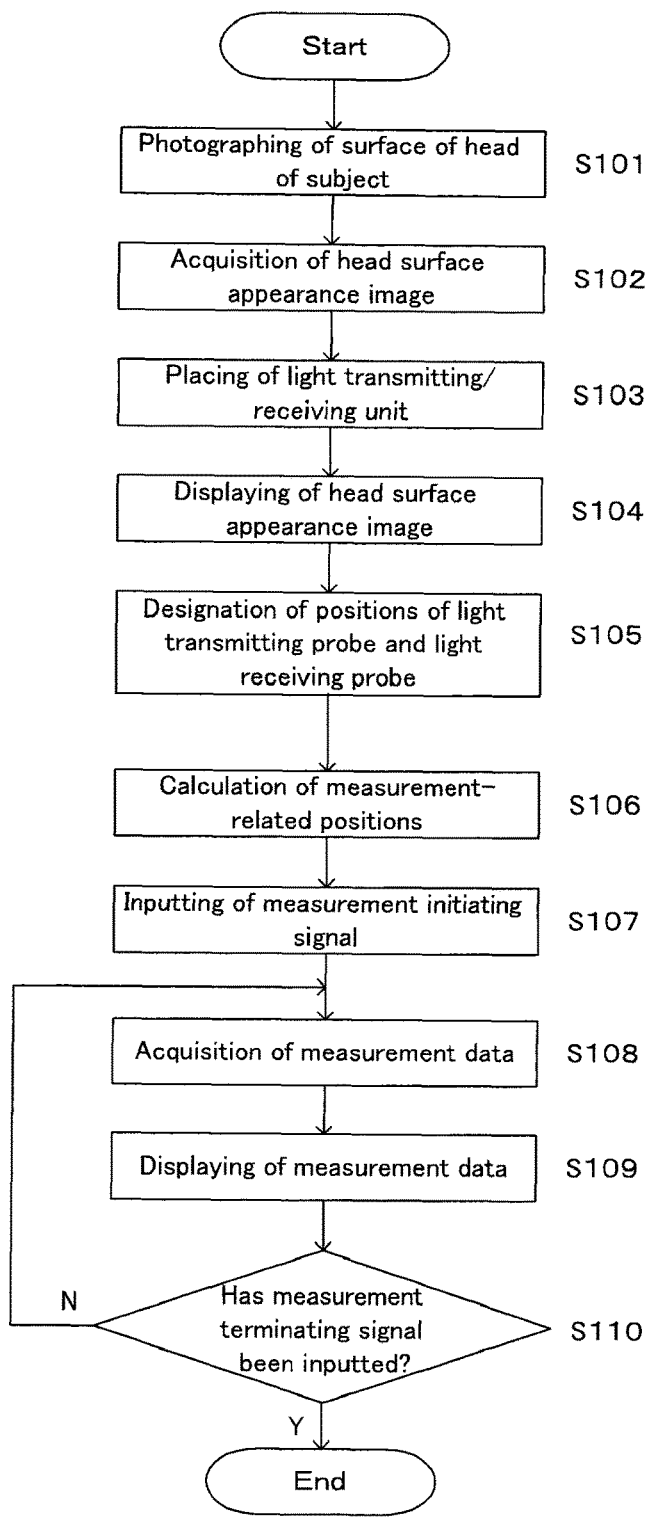
FIG. 4 is a flow chart for illustrating an example of a display method according to the organism optical measurement device.

Next, the display method according to which the organism optical measurement device 1 displays the measurement data is described. FIG. 4 is a flow chart for illustrating an example of the display method in the organism optical measurement device 1.

First, in the process in Step S101, the doctor or the like photographs the surface of the head of a subject using the camera 4.

Next, in the process in Step S102, the head surface appearance image acquiring unit 32 acquires a head surface appearance image from the camera 4 and stores the image in the image data storage area 53. Next, in the process in Step S103, the doctor or the like places the light transmitting/receiving unit 11 on the surface of the head of the subject.

Next, in the process in Step S104, the head surface appearance image display control unit 33 displays the head surface appearance image 24a on the screen 23a.

Next, in the process in Step S105, the doctor or the like designates the positions of nine light transmitting probes 12a to 12i and the eight light receiving probes 13a to 13h in the head surface appearance image 24a by means of the pointer while checking the light transmitting/receiving unit 11 placed on the surface of the head of the subject.

Next, in the process in Step S106, the measurement related position calculating unit 35 calculates a measurement-related position on the head surface appearance image 24a when the predetermined position in the head surface appearance image 24a is designated by the pointer.

Next, in the process in Step S107, the doctor or the like inputs a measurement initiating signal using the input devices 22.

Next, in the process in Step S108, the light emission control unit 42 and the light detection control unit 43 output a drive signal to the light emitting unit 2, and at the same time, receives a light receiving signal (measurement data)

from the light detecting unit 3, and thus stores the measurement data in the measurement data storage area 52.

Next, in the process in Step S109, the measurement data display control unit 37 displays pieces of measurement data #1 to #24 in the measurement-related positions on the basis of the measurement data stored in the measurement data storage area 52 and the measurement-related positions.

Next, in the process in Step S110, the doctor or the like determines whether or not a measurement terminating signal is inputted by using the input devices 22. When it is determined that the doctor or the like has not inputted a measurement terminating signal using the input devices 22, the procedure returns to the process in Step S108.

Meanwhile, in the case where it has been determined that the doctor or the like has inputted a measurement terminating signal using the input devices 22, the flow chart is completed.

As described above, the organism optical measurement device 1 allows pieces of measurement data #1 to #24 to be overlapped on the head surface appearance image 24a when displayed in the measurement-related positions, and therefore, the measured portions in the brain from which the pieces of measurement data #1 to #24 are obtained and whether or not the pieces of measurement data #1 to #24 are precise can be easily understood while checking the head surface appearance image 24a and the pieces of measurement data #1 to #24.

Figure 5:
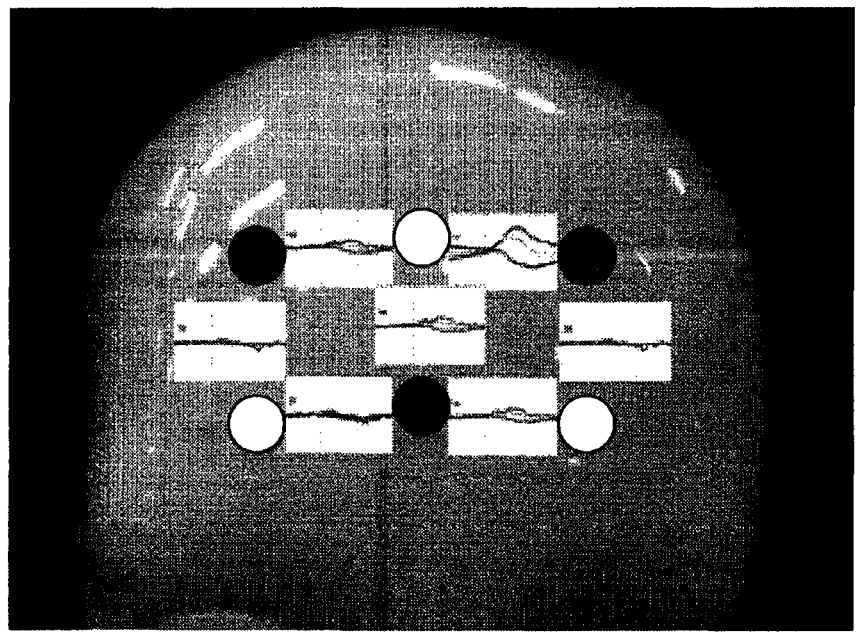
FIG. 5 is a diagram showing another example of a monitor screen for the display in the organism optical measurement device according to the present example.
Figure 6:
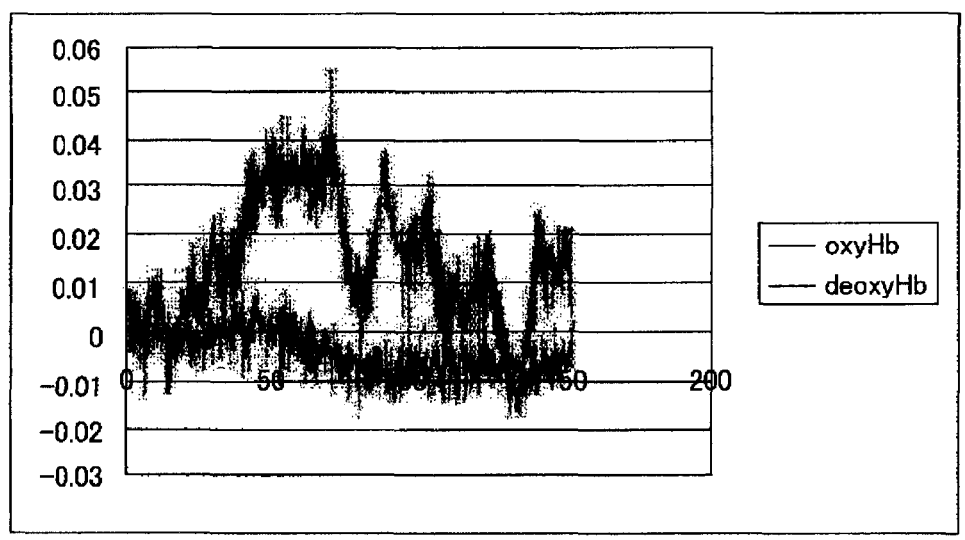
FIG. 6 is a graph showing an example of measurement data.
Figure 7:
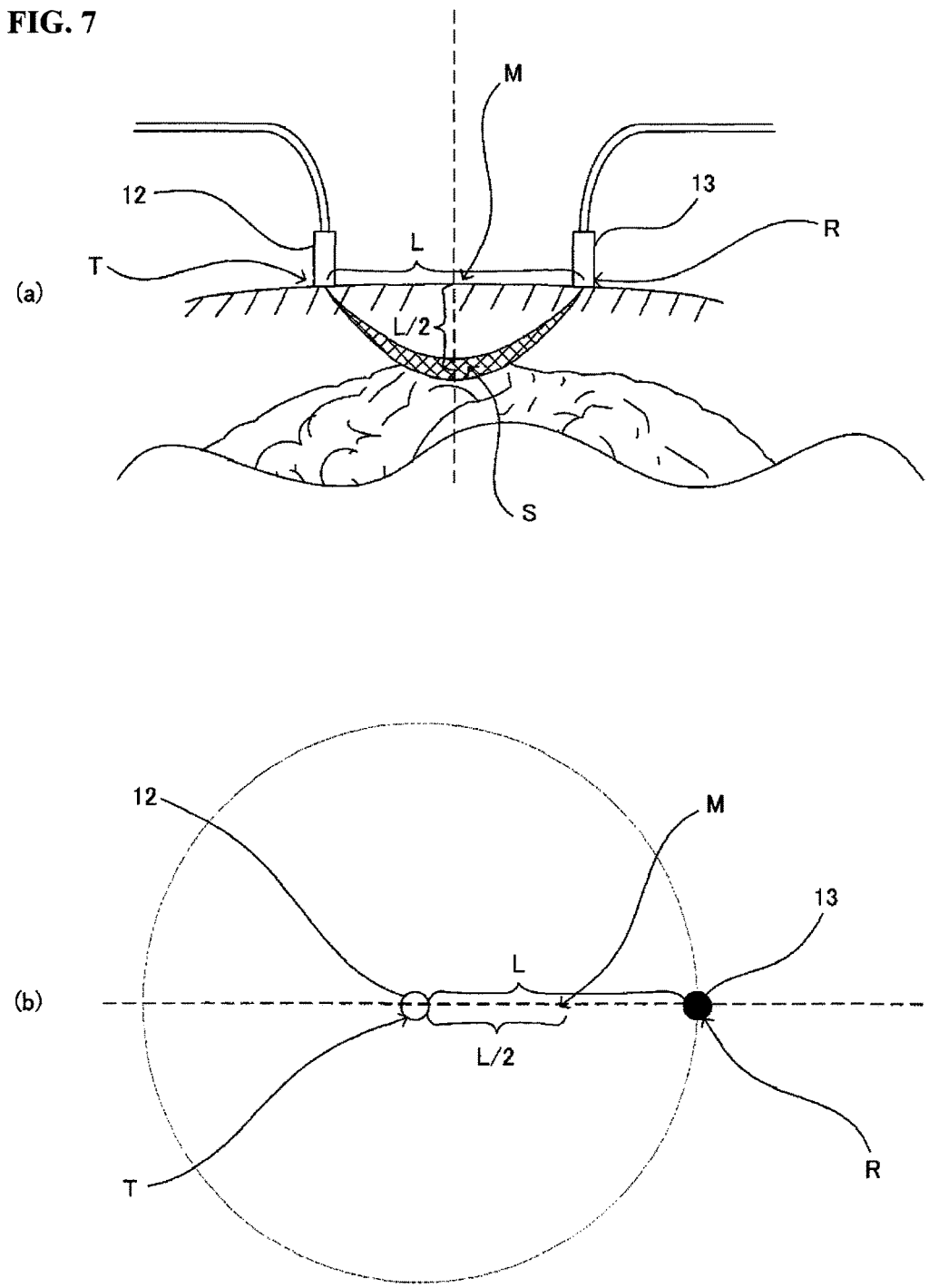
FIGS. 7(a) and 7(b) are diagrams showing the relationship between the measured portion in the brain and a pair of a light transmitting probe and a light receiving probe.
Figure 8:
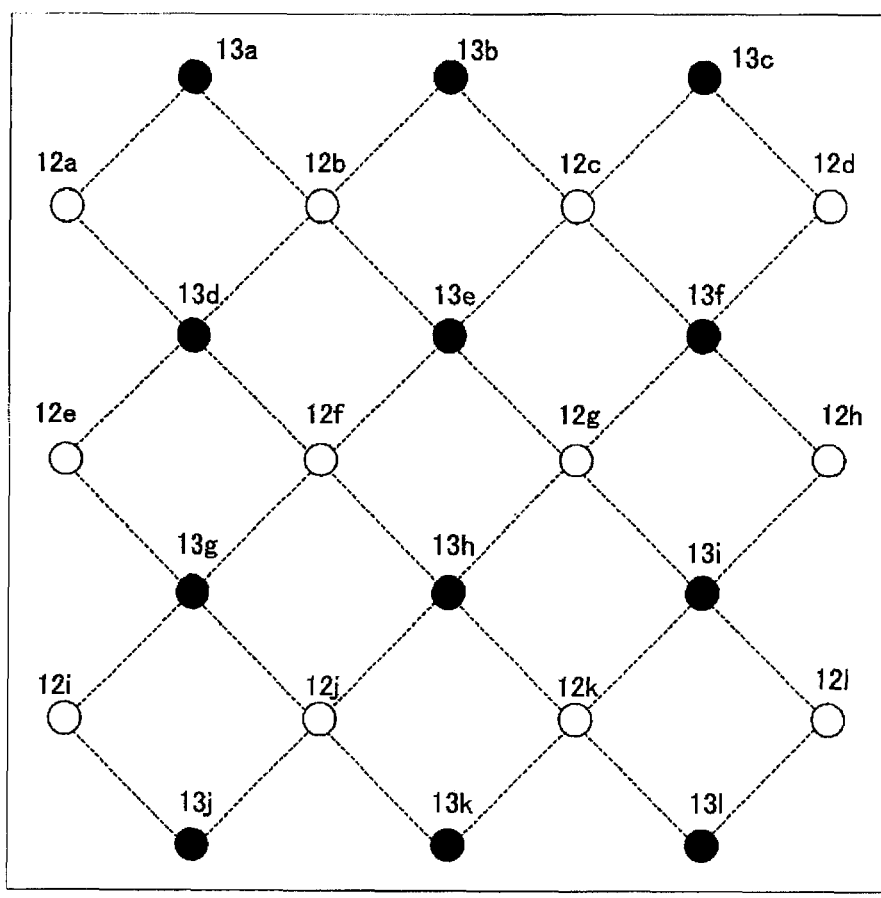
FIG. 8 is a plan diagram showing the positional relationships between 12 light transmitting probes and 12 light receiving probes.
Figure 9:
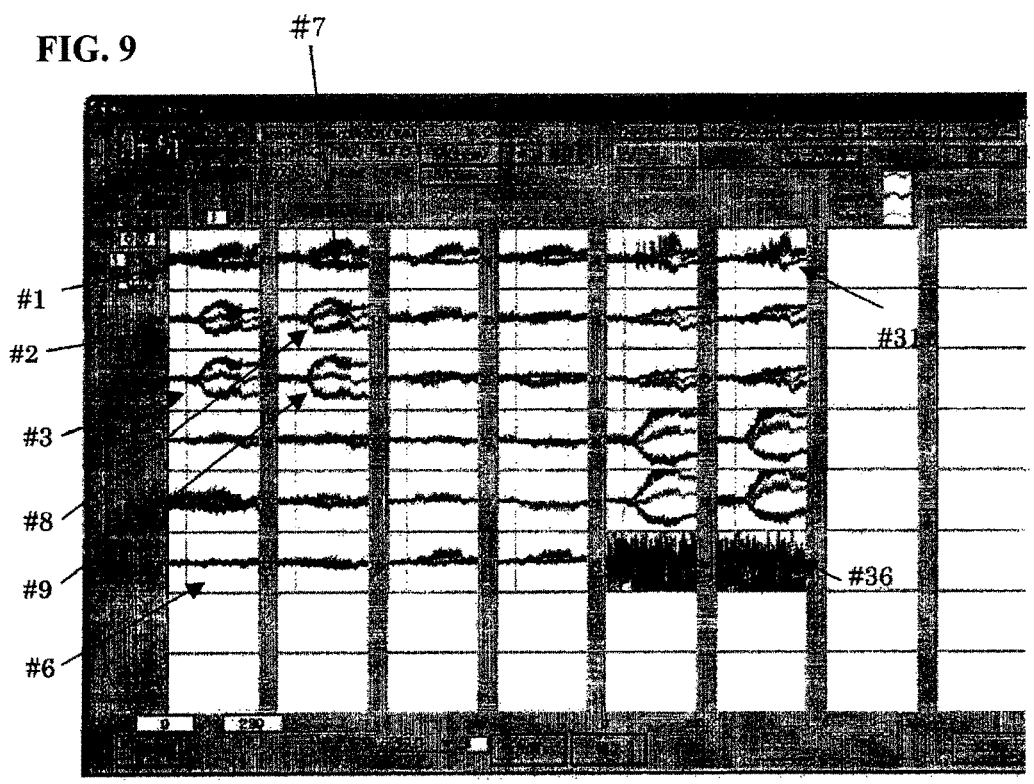
FIG. 9 is a diagram showing an example of a monitor screen displaying 36 pieces of measurement data in a conventional organism optical measurement device.

Though a light transmitting/receiving unit 11 having nine light transmitting probes 12a to 12i and eight light receiving probes 13a to 13h is provided in the above-described organism optical measurement device 1, a light transmitting/receiving unit may have different numbers of light transmitting probes and light receiving probes, for example, three light transmitting probes and three light receiving probes (see FIG. 5).

The present invention can be applied to an oxygen monitor with which a chronological change in the blood flow in the respective portions in the brain and a chronological change in the supply of oxygen can be measured so that it can be diagnosed whether or not tissue of a living body is normal.

The invention claimed is:

1. An organism optical measurement device, comprising:
a light transmitting/receiving unit having a number of light transmitting probes configured to be disposed on a surface of a head of a subject and a number of light receiving probes configured to be disposed on the surface of the head;
a camera which captures an image of the surface of the head on which no light transmitting probes and light receiving probes are disposed; and
a processor configured to:
receive, from the camera, the image of the surface of the head on which no light transmitting probes and light receiving probes are disposed, the image being captured before the light transmitting probes and the light receiving probes are disposed on the surface of the head of the subject;
control a display to display the received image of the surface of the head on which no light transmitting probes and light receiving probes are disposed;
receive a designation of positions on the image of the surface of the head, the positions corresponding respectively to positions where the light transmitting probes and the light receiving probes are attached on the head;
calculate, for each combination of a light transmitting probe and a light receiving probe of the transmitting/receiving unit, a middle point of a shortest line connecting a designated position corresponding to the light transmitting probe of the combination and a designated position corresponding to the light receiving probe of the combination on the image of the surface of the head;
obtain measurement data on brain activities by controlling said light transmitting probes and said light receiving probes so that said light transmitting probes irradiate the surface of the head with light and said light receiving probes detect light emitted from the surface of the head;
control the display to display, for each combination of the light transmitting probe and the light receiving probe, the measurement data at the corresponding middle point on the image of the surface of the head; and
monitor a change in blood flow in the respective measurement sites based on the obtained measurement data in order to diagnose abnormality of tissue of a living body.

2. The organism optical measurement device according to claim 1, said measurement data is data showing a chronological change in the concentration of hemoglobin.

3. The organism optical measurement device according to claim 1, further comprising image data storage for storing the image of the surface of the head on which no light transmitting probes and light receiving probes are disposed.

4. An organism optical measurement method comprising:
receiving an image of a surface of a head of a subject on which no light transmitting probes and no light receiving probes are placed, the image being captured before light transmitting probes and light receiving probes are placed on the surface of the head of the subject;
placing a light transmitting/receiving unit having light transmitting probes and light receiving probes on the surface of the head of the subject;
designating sites on the image of the surface of the head on which no light transmitting probes and no light receiving probes are placed, the sites corresponding respectively to sites of where the light transmitting probes and the light receiving probes are attached on the head,
calculating, for each combination of a light transmitting probe and a light receiving probe of the transmitting/receiving unit, a middle point of a shortest line connecting a designated position corresponding to the light transmitting probe of the combination and a designated position corresponding to the light receiving probe of the combination on the image of the surface of the head;
obtaining the measurement data on brain activities by controlling the light transmitting probes and the light receiving probes so that said light transmitting probes irradiate the surface of the head with light and said light receiving probes detect light from the surface of the head;
displaying, for each combination of the light transmitting probe and the light receiving probe, the measurement data at the corresponding middle point on the image of the surface of the head; and
monitoring a change in supply of oxygen in the respective measurement sites based on the obtained measurement data in order to diagnose abnormality of tissue of a living body.

* * * * *